(12) United States Patent
Gilyanna

(10) Patent No.: US 8,790,323 B1
(45) Date of Patent: Jul. 29, 2014

(54) BLOOD CONTAINMENT SLEEVE

(76) Inventor: Nelson Gilyanna, Rocky Hill, CT (US)

( * ) Notice: Subject to any disclaimer, the term of this patent is extended or adjusted under 35 U.S.C. 154(b) by 117 days.

(21) Appl. No.: 13/506,043

(22) Filed: May 24, 2012

Related U.S. Application Data

(60) Provisional application No. 61/479,102, filed on Apr. 26, 2011.

(51) Int. Cl.
*A61B 19/00* (2006.01)

(52) U.S. Cl.
USPC .................................................. 604/356

(58) Field of Classification Search
USPC ........................................ 604/385.24; 2/270
See application file for complete search history.

(56) References Cited

U.S. PATENT DOCUMENTS

| | | | | |
|---|---|---|---|---|
| 1,517,984 A * | 12/1924 | Ole | ...................................... | 2/59 |
| 4,856,112 A * | 8/1989 | Effle | ................................... | 2/59 |
| 5,003,970 A * | 4/1991 | Parker et al. | ..................... | 602/50 |
| 5,312,385 A * | 5/1994 | Greco | ............................ | 604/356 |
| 5,817,038 A * | 10/1998 | Orange et al. | ................... | 602/3 |
| 6,148,444 A * | 11/2000 | Holmes et al. | ........................ | 2/69 |
| 6,216,270 B1 * | 4/2001 | Moquin et al. | ....................... | 2/69 |
| D457,290 S * | 5/2002 | Thompson | ..................... | D2/743 |
| 6,832,611 B2 * | 12/2004 | Altman | .......................... | 128/846 |
| 8,529,481 B1 * | 9/2013 | Lois | .................................. | 602/3 |
| 2003/0150044 A1 * | 8/2003 | Hoy | .................................. | 2/125 |
| 2005/0027227 A1 * | 2/2005 | Dumas et al. | ................... | 602/41 |
| 2006/0010663 A1 * | 1/2006 | Szypka | ............................ | 27/28 |
| 2008/0235846 A1 * | 10/2008 | Schossberger et al. | ............ | 2/59 |
| 2010/0095587 A1 * | 4/2010 | Marks | ................................ | 47/72 |

* cited by examiner

*Primary Examiner* — Susan Su

(57) ABSTRACT

A blood containment sleeve of any material and in any form with a cut in it, that dialysis patients wear, preferably, on their arm. The sleeve allows for the dialysis to be carried on and contains the blood spill. Main ideas disclosed are the cut in the sleeve and the containment of the patient's blood. The cut on the sleeve may be a simple cut or a cut with a zipper. The sleeve can have elastic closures at both ends. The sleeve may be by itself or on a shirt, jacket or any other apparel.

1 Claim, 1 Drawing Sheet

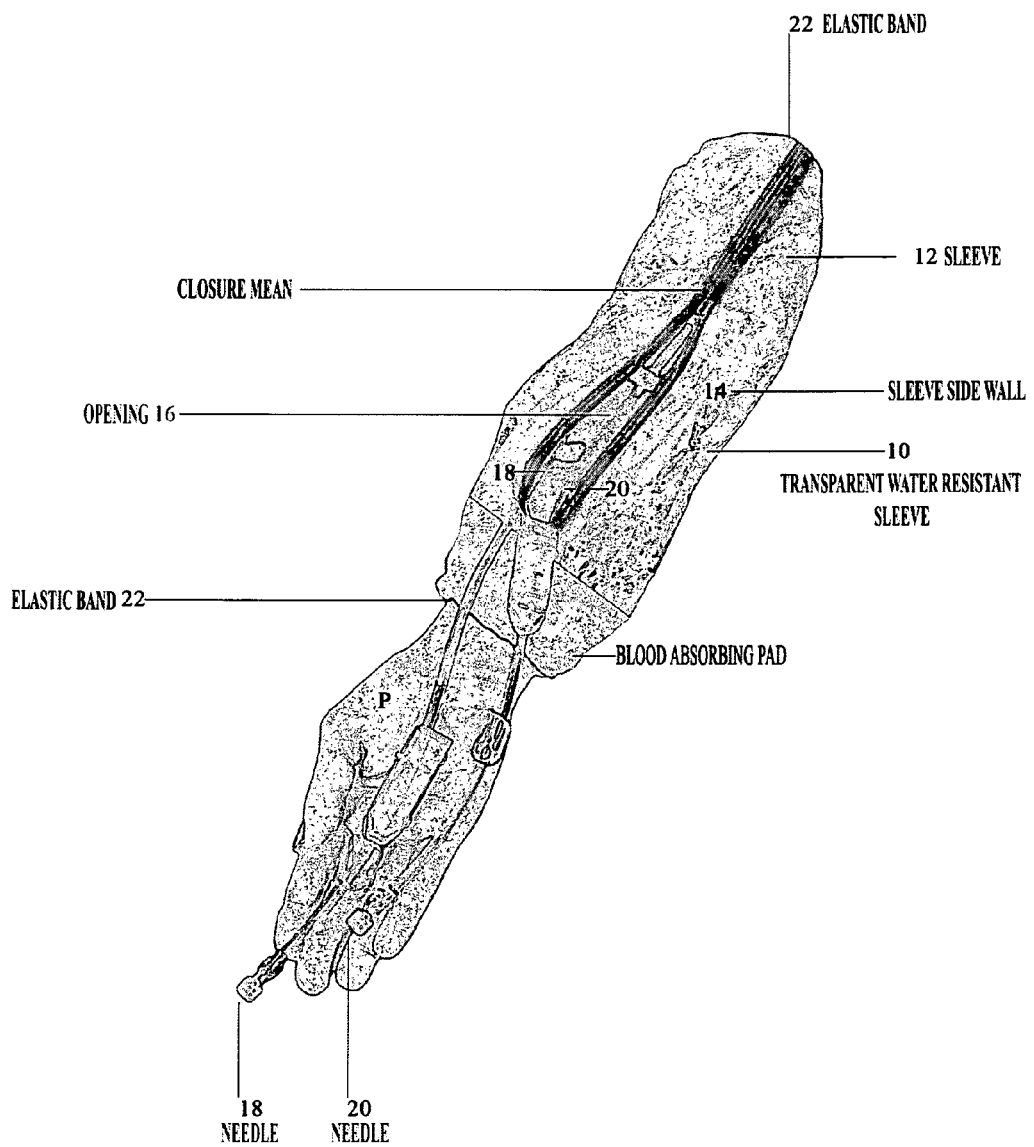

BLOOD CONTAINMENT SLEEVE

CROSS-REFERENCE TO RELATED APPLICATIONS

This application claims the benefit of provisional patent application Ser. No. 61/479,102 filed on Apr. 26, 2011 by present inventor.

BACKGROUND OF THE DISCLOSURE

1. Field of the Disclosure

This disclosure is for use in the medical field to protect clothing and upholstery from contamination from exposure to blood. The disclosure is useful particularly in connection with the medical practice of dialysis, inoculation, transfusion, and blood analyses.

2. Description of Related Art

During dialysis, two needles are inserted into an access called Fistula or Graft, usually in the arm. Sometimes, one or both of the needles is inadvertently dislodged, causing bleeding. Also, when the needles are removed, the nurse or patient must manually compress the needle's sites for ten minutes to allow time for clothing. If done incorrectly, excessive bleeding occurs.

In either one of the above events, there are several potential, negative consequences. First, blood flows to the chairs or surface upon which the patient sits. (The majority of state health citations for infection control have to do with blood contaminations, most notably occur on chairs). Second, blood drains onto patient's clothes, which ruin fabrics, upsets patients, and presents a potential health hazard when the patient leaves the care unit.

SUMMARY OF THE DISCLOSURE

The present disclosure provides a blood containment sleeve, preferably in the form of a water proof or water resistant tubular sleeve that is worn on the arm of a dialysis patient. The main purpose of the blood containment sleeve is to capture and contain blood that flows from the patient's venipuncture. The sleeve is kept in place on the patient's arm by an elastic band at each end of the sleeve. However, the device may alternatively have one elastic band at only one end of the sleeve, or no elastic band at all.

The sleeve typically is, but need not be from about 8 to about 24 inches long. The sidewall of the sleeve preferably has a cut or an opening of any suitable size, for example, from about 5 to about 8 inches along the longitudinal axis of the sleeve. The opening can be a simple cut of from about 2 to about 4 inches wide to allow access to the needle(s) and allow for easy manual compression of the patient's artery. The cut or opening should be wide enough to visually monitor and follow the travel and/or position of the blood within the sleeve.

The blood contamination sleeve of the disclosure can be made of any suitable material and can be in any suitable color. Preferably the color is light, for example, white, to contrast and see the color of the blood. This feature will help the attendants notice any bleeding during the analysis. In addition, the sleeve opening and material will help in making sure that needle access is visible during dialysis. Should blood flow from the patient's arm, the blood collects or pools at the bottom interior surface of the preferably loose fitting sleeve, sparing contamination of the patient's clothing and chair. The bottom surface can have a sponge, foam coating, cotton or other pad disposed above or below at least a portion of the interior surface of the blood containment sleeve to absorb and/or contain loose blood until disposal of the sleeve.

The blood containment sleeve is made of any suitable material that is water proof or water resistant and that is capable of containing blood. The material, preferably, is transparent to enable an attendant to monitor the dialysis, blood flow and containment.

The opening in the sidewall of the blood containment sleeve may or may not have one or more closeable closures to close or vary the size of the opening to contain blood within the sleeve. Preferably, the entire sleeve and/or closure is transparent. The closeable closure can be openable and closeable to vary the size of the opening by use of one or more metal or plastic zippers, Zip-locks, as used on flexible plastic packages, or for example, hook and loop Velcro closure system.

The sleeve of the disclosure is made of any suitable material such as poly-ethylene, Vinyl, Urethane, Neoprene or Denim, and the like.

The sleeve of the disclosure may be regular or sterilized. The sleeve may be supplied in packages of different quantities, or as individually packed or supplied through a dispenser.

Sleeves of the disclosure include sleeves with slots on jackets and shirts.

Sleeves of the disclosure may be used for other purposes where blood containment is necessary.

BRIEF DESCRIPTION OF THE DRAWINGS

FIG. 1 is a front perspective view of an exemplary embodiment of a blood containment sleeve of the present disclosure, the sleeve being shown on and along a patient's forearm, with an opening in the sidewall and a patient's palm, each facing upward. (The patient's upper arm is not shown).

Referring to FIG. 1, there is provided a blood containment sleeve, generally designated 10, preferably in the form of water proof or water resistant tubular sleeve 12. Sleeve 12 is worn on the forearm of a dialysis patient P. Sleeve 12 has a sidewall 14, and preferably an opening 16 formed in the sidewall and showing, for example, two needles 18, 20, in place inside sleeve 12 during the dialysis procedure. FIG. 1 shows the forward and back end portions of sleeve 12 each having an elastic band 22 that holds sleeve 12 to the patient's right forearm. Sleeve 12 need not be, but preferably is transparent and shows the interior of sleeve 12, and tubes, e.g., 18, 20, inside sleeve 12. Sleeve 12 clearly shows its inside through opening 16 or through a transparent door (not shown).

It is clear from the description above that while or in connection with performing dialysis on patients, blood may spill on patient's clothes, furniture and surroundings. To contain the blood spill and hence clean it more easily, there is disclosed herein a sleeve preferably with a cut in it and that patients wear on their arms. The sleeve allows the dialysis or other needles to be placed on the patient and contain the blood spill to the inside of the sleeve. Also, it is easier to notice the blood spill and clean it.

It should be understood that the forgoing description is only illustrative of the present disclosure. Various alternatives and modifications can be devised by those skilled in the art without departing from the disclosure. Accordingly, the present disclosure is intended to embrace all such disclosures, modifications, and variances that fall within the scope of the disclosure.

I claim:

1. A limb covering for containing blood spill from a patient undergoing dialysis, said covering consisting of:

a transparent waterproof or water-resistant sleeve configured to loosely encircle a portion of a limb of the patient;

an elastic band disposed at each end of the sleeve to keep the sleeve in place on the patient's limb;

an opening through an entire thickness of a side wall in the sleeve, the opening configured for access of a needle used in the dialysis;

a closure means configured to vary a size of the opening;

an absorbent material disposed on a bottom interior surface of the sleeve to collect blood flowing from the patient's limb while the sleeve is encircling the patient's limb.

\* \* \* \* \*